(12) United States Patent
Hysmith (10) Patent No.: US 7,374,786 B2
(45) Date of Patent: May 20, 2008

(54) BIOIMMUNE-AGGRESSIN COMPOSITION FOR SUPPRESSION OF XANTHOMONAD INFECTIONS IN AGRICULTURE CROPS

(75) Inventor: Robert M Hysmith, Clearwater, FL (US)

(73) Assignee: Biosys Corporation, Clearwater, FL (US)

( * ) Notice: Subject to any disclaimer, the term of this patent is extended or adjusted under 35 U.S.C. 154(b) by 254 days.

(21) Appl. No.: 10/755,093

(22) Filed: Jan. 9, 2004

(65) Prior Publication Data

US 2005/0153005 A1 Jul. 14, 2005

(51) Int. Cl.
*A61K 36/00* (2006.01)
*A01N 65/00* (2006.01)

(52) U.S. Cl. ..................... 424/773; 424/774
(58) Field of Classification Search ............. 435/910, 435/254.6
See application file for complete search history.

(56) References Cited

U.S. PATENT DOCUMENTS

| | | | |
|---|---|---|---|
| 4,724,147 A | 2/1988 | Marois et al. | |
| 4,900,348 A * | 2/1990 | Hoitink | 71/6 |
| 5,165,928 A | 11/1992 | Smith et al. | |
| 5,268,173 A | 12/1993 | Howell et al. | |
| 5,290,557 A * | 3/1994 | Mason et al. | 424/410 |
| 5,639,794 A * | 6/1997 | Emerson et al. | 514/699 |
| 5,726,167 A | 3/1998 | Dodge et al. | |
| 5,882,915 A | 3/1999 | Howell | |
| 5,968,504 A | 10/1999 | Tahvonen et al. | |
| 6,077,506 A | 6/2000 | Marrone et al. | |
| 6,139,839 A | 10/2000 | Odell et al. | |
| 6,242,420 B1 | 6/2001 | Hanson et al. | |
| 6,251,951 B1 | 6/2001 | Emerson et al. | |
| 6,277,823 B1 | 8/2001 | Kramer et al. | |
| 6,326,016 B2 * | 12/2001 | Moesinger | 424/405 |
| 6,475,772 B1 * | 11/2002 | Kalra et al. | 435/254.6 |
| 6,482,770 B2 | 11/2002 | Dutcheshen et al. | |
| 2002/0015988 A1 * | 2/2002 | Enzmann et al. | 435/252.1 |
| 2002/0038005 A1 | 3/2002 | Wojciechowska et al. | |
| 2002/0136754 A1 | 9/2002 | Short et al. | |

OTHER PUBLICATIONS http://www.answers.com/topic/genus-xanthomonas.*
Deutsche Sammlung von Mikroorganismen und Zellkulturen GmbH (DSMZ), Bacterial Nomenclature Up-To-Date, p. 85 (Apr. 2006).*
Belanger, R.R., Bowen, P.A., Ehret. D.L. et al. Soluble silicon: Its role in crop and disease management of green house crops, Plant Disease, 1995.79:329-336.
Bingham, R., Bellew, B.A., Bellew J.G., Yucca plant saponin in the management of arthritis, J. Appl Nutr, 1975, 27:45-50.
Bradbury, J.F., Xanthomonas Dowson 1939, Bacteria, 1986, 187. pp. 198-260, CAB International Mycological Institute, Slough, England.

(Continued)

*Primary Examiner*—Johann Richter
*Assistant Examiner*—Ernst V Arnold
(74) *Attorney, Agent, or Firm*—David W. Pettis, Jr., P.A.

(57) ABSTRACT

A composition for treating *Xanthomonas* spp. infections in agriculture crops wherein the treatment composition is an admixture of *T. harzianum*, *Y. schidigera* root extract, *Y. schidigera* leaf extract, and *X.* spp. extract. The composition is also efficacious as a pre-infection agent for enhancing the resistance of agriculture crops to such infections. The composition is preferably applied by spraying.

9 Claims, 1 Drawing Sheet

OTHER PUBLICATIONS

Brukner, H., Methods for the rapid detection, isolation and sequence determinatuon of Peptaibols and other aib-containing peptides of fungal origin, Chromatographia, 1984, 19:188-199.

Delaney, T.P., Genetic dissection of acquired resistance to disease, Plant Physiol., 1997, 113:5-12.

De La Cruz, J. Pintor-Toro, J.A., Benitez, T., and Llobell, A., Purification and characterization of an endo-B-1.6-glucanese from Trichoderma harzianum that is related to its mycoparasitism, J. Baceriol, 1995, 177: 1864-1871.

Dong. H. and Beer, S.V., Riboflavin induces disease resistance in plants by activating a novel signal transduction pathway, Phylopathology. 2000, 90:801-811.

El Hajji. M., Rebuffat, S.. Lecommandeur, D., and Dodo. B., Isolation and sequence determination of trichorzianines A antifungal peptides, Trichoderma harzianum. Int. J. Peptide Protein Res., 1987, 29:207-215.

Epstein, E., The anomaly of silicon in plant biology, Procl. Natl. Acad. Sci., 1994, 91:11-17, U.S.A.

Fawe, A.. Abouu-Zaid, M., Menzies. J.G. et al. Silicon-mediated accumulation of flavonoid phyloalexins in cucumber, Phylopathology, 1998.88:396-401.

Gardan, L.. Brault. T., and Germain E., Copper resistance of *Xanthomonas campestris* pv. juglands in French Walnut orchards and its association with conjugative plasmids, Acta Hort., 1993. ISHS, 311:239-265.

Ghisalberti, E.L., and Sivasithamparan, K., Antifungal antibiotics produced by *Trichoderma* spp, Soil Biol. Biochem., 1991, 23:1011-1021.

Gottwald, T. R., Graham, J.H., and Riley T.D., The influence of spray adjuvants on exacerbation of citrus bacterial spot. Plant Disease, 1997.81:1305-1310.

Habte, M. and Alexander, M., Protozoa as agents responsible for the decline of *Xanthomonas campestris* in soil, Appl. Microbiol., 1975, 29(2):159-164.

Han, D., Y., Colin, D.L., Bauer, W.D., Hoitink H.A.J., A rapid bioassay for screening rhizosphere microorganisms for their ability to induce systemic resistance, Phytopathology.2000, 90:327-332.

Hartwell, J.L., Types of anticancer agents isolated from pants. Cancer Treat Rep., 1976, 60:1031-1067.

Hasan. S.B., Trichoderma Harzianum Rifai Strain T-39; Exemption from the Requirements of a Tolerance,Federal Register,2000,pp. 38753-38757.65:121.

Howell. C.R.. and R.D. Stipanovic, Phytotoxicity to crop plants and herbicidal effects on weeds of viriodiol produced by Gliocladium virens, Phytopathology, 1984. 74:1346-1349.

Howell, C.R., and Stipanovic R.D.,Effect of sterol biosynthesis inhibitors on phytotoxin (viridin) production by Gliocladium virens in culture, Phytopathology. 1994, 84:969-972.

Jabs, T., Tschope. M., Colling, C., et al, Elicitor-stimulated ion fluxes and O2 from oxidative burst are essential components of triggering defense gene activation and phytoalexin synthesis in parsley, Proc. Natl. Acad. Sci.. 1997, 94:4800-4805, USA.

Uda A. Sanekata, M.. Fugita, T. et al, Fungal metabolites XVI. Structure of new peptaibols, trichorzins I-VI from the fungus *Trichoderma harzanium*, Int. J Peptide Protein Res., 1987, 29:207-215.

Imaizumi, S.. Tateno, A.. Morita, K.. Fujimori. T., Seasonal factors affecting the control of annual bluegrass (Poa annua L.) with *Xanthomonas campestris* pv. poae., Biol. Control, 1999, 16(1):18-26.

Jones. R.W. and Hancock, J.G.. Conversion of viridin to viridiol by viridin-producing fungi, Can J Microbiol. 1987, 33:962-966.

Kloepper, J.W., Tuzun. S., Kuc, J.A., Proposed definitions related to induced disease resistance, Biocontrol Sci. Technol., 1992, 2:349-351.

Ojanen, T., Helander, I.M., Haahtela, H., et al., Outer membrane proteins and lipopolysaccharides in pathovars of *Xanthomonas campestris*, Appl. Environ. Microbiol., 1993, 59:4143 (Abstr.).

Ozores-Hampton, M.O. and Obreza. T.A., A composted waste use on Florida Crops: A Review, International Composting Symposium, 2000. Nova Scotia.

Pruvost. O., Boher, B., Brocherieux, M.. et al., Survival of *Xanthomonas axonopodis* pv. citri in leaf lesions under tropical environmental conditions and simulated splash dispersal of inoculum, Phytopathology, 2001, 92:336-346.

Raupach. G.S., Liu, L. Murphy K.F.. et al., induced systemic resistance in cucumber and tomato against cucumber mosaic cucumovirus using plant growth-promoting rhizobacteria, Plant Disease. 1996, 80:891-894.

Rebuffat. S., El Hajji, M., Henning, P. et al.. Isolation sequence and conformation of seven trichorzianines B from *Trichoderma harzianum*, Int J Protein Peptide Res., 1989, 34:200-210.

Reyes A.A., Suppression of Fusarium and Pythium pea root rot by antagonistic microorganisms, Phytoprotect., 1985, 66:23-29.

Sawa. R., Mori, Y., Inuma, H.. Harzianic acid, a new microbial antibiotic from a fungas, J. Antibiotics, 1994, 47:731-732. Tokyo.

Scarpato, R., Bertoli, A.. Baccarati A., et al., Different effects of newly isolated saponins on the mutagenicity and cytotoxicity of the anticancer drugs mitomycin C and bleomycin in human lymphocytes, Mutat. Res.. 1998, 420:49-54.

Schubert T.S., RIZVL.S.A., Sun, X et al., Meeting the challenge of eradicating citrus canker in Florida—Again, Plant Disease, 2001, 85:340-356.

Wei. G., Kloepper, J.W., Tuzun, S., Induction of systemic resistance of cucumber to *Colletotrichum orbiculare* by select strains of plant growth promoting rhizobacteria, Phytopathology, 1991, 81:1508-1512.

Werner. D. and Roth R., Silica metabolism. Inorganic Plant Nutrition, 1983, pp. 683-694, Sringer-Verlag, Berlin.

Young. K.M.. Due D.W.. Bradbury J.F. et al., A proposed nomenclature and classification for plant pathogenic bacteria, N.Z. J Agric Res., 1978, 21:153-177.

Zhoa, Y.. Christensen, S.K., Frankhauser, C.. et al., A role for flavin monooxygenaslike enzymes in auxin biosynthesis, Science, 2001, 291:306-309.

Ziegler, D.M., Flavin-containing monooxygenases: enzymes adapted for multisubstrate specificity, Trends in Pharmacol. Sci., 1990, 11:321-324.

Ziegler, D.M., Recent studies on the structure and function of multisubstrate flavin-containing monooxygenases, Ann. Rev. Pharmacol. Toxicology, 1993,33:179-199.

Zubrzycki, H.M. and Diamante, D.Z.A., Relationship between the amount of the inoculum and the infection caused by *Xanthomonas campestris* pv. citri on citrus seedlings through natural infections in the field. Proc. Int Soc. Citriculture, 1987, pp. 379-382, Sao Paulo,Brazil.

Cubero, J., Graham, J.H.. Genetic Relationship among Worldwide Strains of *Xanthomonas* Causing Canker in Citrus Species and Design of New Primers for Their Identification ny PCR, Applied and Envir. Microbiology, 2002, 68.3: 1257-1264.

Koike. Steven T., Azad, Hamid R., and Cooksey, Donald A., *Xanthomonas* Leaf Spot of Catnip: A New Disease Caused by a Pathovar of *Xanthomonas campestris*, Plant Disease. 2001, pp. 1157-1159, Pub. No. D-2001-0904-01R, The Amer. Phyto. Soc.

Liu. L., Kloepper, J.W., and Tuzan, S., Induction of Systemic Resistance in Cucumber Against Bacterial Angular Leaf Spot by Plant Growth-Promoting Rhizobacteria Phytopathology, 1995, 85:8, pp. 843-847, The Amer. Phyto. Soc.

Rott, P., Mohamed, I.S., Klett, P., Soupa, D., De Saint-Albin, A., Feldmann, P.. and Letourmy, P., Resistance to Leaf Scald Disease Is Associated with Limited Colonization of Sugarcane and Wild Relatives by *Xanthomonas albilineans*, Phytopathology, 1997, 87: 12, pp. 1202-1213.

Severn, W.B., Kelly, R.F., Richards, J.C., and whitfield. C., Structure of the core oligosaccharide in the serotype O8 lipopolysaccharide from *Klebsiella pneumoniae*, J. Bacteriol, 1996, 178:1731-1741.

* cited by examiner

FIGURE 1

BIOIMMUNE-AGGRESSIN COMPOSITION FOR SUPPRESSION OF XANTHOMONAD INFECTIONS IN AGRICULTURE CROPS

FIELD OF INVENTION

The present invention concerns a compounded aggressin derived from a bioextract mixture for controlling and preventing phytopathogenic xanthomonad infections in agriculture related crops. This invention is based on the principles of inducing resistance against phytopathogenic xanthomonads using a combined mixture of bioextracts from non-phytopathogenic *Xanthomonas* spp., *Trichoderma harzianum*, and from the plant *Yucca schidigera*. The method is environmentally safe and affords plant protection against a variety of *Xanthomonas* spp. and their pathovariants.

BACKGROUND OF THE INVENTION

The genus *Xanthomonas* Dowson 1939 compromises a diverse group of gram-negative, obligate aerobic, non-fermentative, rods which are motile by a single polar flagellum, and can produce a brominated yellow pigment identified as xanthomonadin. All reported strains of this genus have been described as plant associated, and most are reported as being pathogenic to a particular plant host. Based on microbiological classification, this genus can be separated into at least five separate species: *X. campestris*, *X. fragariae*, *X. ampelina*, *X. albilineans*, and *X. axonopodis*. [Young, K. M., Due D. W., Bradbury J. F et al. 1978. A proposed nomenclature and classification for plant pathogenic bacteria. N. Z. J Agric Res. 21: 153-177; Vauterin, L., Yang, P., Hoste, B. et al. 1992. Taxonomy of xanthomonads from cereals and grasses, based on SDS-PAGE of proteins, fatty acid analysis and DNA hybridization. *J. Gen. Microbiol.* 138: 1467-1477].

In nature, these bacteria are—in principle—free-living—constituting a broad membership of both rhizospheric and phyllospheric microflora [Vauterin, L., Yang, P., Alverez A. et al. 1996. Identification of non-pathogenic *Xanthomonas* strains associated with plants. *Syst. Appl. Microbiol.* 19:96-105]. Many *Xanthomonas* spp. are known to be phytopathogenic, and can cause devastating agriculture diseases such as citrus canker in a variety of *Citrus* spp.; bacteria leaf spot of citrus; and leaf scaled disease in sugarcane [Bradbury, J. F. 1986. *Xanthomonas* Dowson 1939, 187. Pages 198-260. Bacteria. CAB International Mycological Institute, Slough, England].

Whereas a considerable number of publications exist regarding the genetic virulence factors associated with pathogenic species of *Xanthomonas*, a paucity exists within the literature regarding the principle mode of invasion and biofilm interactions for colonization. The most likely points of invasion of pathogenic strains of *Xanthomonas* spp. involve access via the stomata or through portals of injury to either the plant leaves or fruit [Zubrzycki, H. M. and Diamante, D. Z. A. 1987. Relationship between the amount of the inoculum and the infection caused by *Xanthomonas campestris* pv. *citri* on citrus seedlings through natural infections in the field. Pages 379-382 in: *Proc. Int. Soc. Citriculture*, Sao Paulo, Brazil; and Schubert T. S., Rizvl, S. A. Sun, X et al. 2001. Meeting the challenge of eradicating citrus canker in Florida—Again. Plant Disease 85: 340-356]. However, natural invasion through stomata may require a higher inoculum source. Such concentrations are higher than what normally could be achieved under a healthy phyllosphere condition [Pruvost, O., Boher, B., Brocherieux, M., et al. 2001. Survival of *Xanthomonas axonopodis* pv. *citri* in leaf lesions under tropical environmental conditions and simulated splash dispersal of inoculum. *Phytopathology* 92: 336-346]. Thus—not being delimited by theory—the principle mode of invasion of such organisms may be primarily due through injured areas of the plants. Such injuries could occur via mechanical means or through insect engendered injury.

Current methods of controlling plant infections by *Xanthomonas* spp. include the use of copper containing sprays. Likewise such sprays have been utilized to cosmetically change the appearance of canker lesions on certain citrus fruits. However, the use of such sprays is delimiting due to their toxicity. Furthermore, some *Xanthomonas* spp. have become resistant to such copper controlling agents [Gardan, L., Brault, T., and Germain E. 1993. Copper resistance of *Xanthomonas campestris* pv. *juglands* in French walnut orchards and it association with conjugative plasmids. Acta Hort. (ISHS) 311:239-265]. Thus, a priori conclusions suggests that many *Xanthomonas* spp. may express resistance to copper sprays. This may not be exclusive of *X. axonopodis* [pv.] *citri*—the etiological agent of citrus canker. Furthermore, it has been suggested that utilization of such spraying methods may exacerbate the spread of citrus bacterial spot [Gottwald, T. R., Graham, J. H., and Riley T. D. 1997. The influence of spray adjuvants on exacerbation of citrus bacterial spot. *Plant Disease.* 81:1305-1210].

Most states have adopted considerable eradication programs regarding the control of xanthomonad-related diseases. None is more prevalent than Florida's eradication program targeting citrus canker. Regulated decontamination using a variety of agents is strictly enforced, and Florida incorporates the removal and destruction of infected trees along a specific radius of the infected areas. One concern regarding such methods is that the method of removing such infected trees may aid in the dispersal of the bacterium. Nonetheless, control measures have had limited success and are very expensive to both regulatory bodies and citrus grove owners. Thus alternative measures for expedient and economical control of such diseases are justified.

In nature, many rhizosphere and phyllosphere microflora express characteristics which keep some pathogenic bacteria species in a balance via competition for nutrients or the release of factors which injure or kill possible pathogens. Such characteristics are focused under the concept of biological control. Since the early 1990's, considerable efforts have focused on the control of fungal and bacterial disease using organisms which excrete killing agents directed at such pathogens, or organisms which more fastidiously compete for nutrients against the proposed pathogen—thereby competitively retarding the growth of the more pathogenic species.

Whereas the concept of biological control has been effective in controlling many fungal diseases, biological control has just recently began to focus on xanthomonad-related infections. For example, certain bacterial eating protozoa have been identified within the rhizosphere which control certain pathogenic *Xanthomonas* spp. within the soil in proximity to the host plant [Habte, M. and Alexander, M. 1975. Protozoa as agents responsible for the decline of *Xanthomonas campestris* in soil. *Appl. Microbiol.* 29(2): 159-164]. To date, such organisms have not been employed in fighting xanthomonad-related diseases. In contrast, xanthomonads have been employed as biological control agents to control noxious weeds. *Xanthomonas campestris* pv. *poae* is utilized as a biological control agent of annual bluegrass [Imaizumi, S., Tateno, A., Morita, K., Fujimori, T. 1999. Seasonal factors affecting the control of annual bluegrass (*Poa annua*) with *Xanthomonas campestris* pv. *poae*. *Biol. Control* 16:18-26].

In some cases, invasion of phytopathogenic microbes themselves induce defense mechanisms within plants to prevent further injury. The vast majority of injuries in some agriculture crops do not become infected because of the plant's own defense system. A considerable number of publications present convincing evidence that some rhizosphere microorganisms can induce systemic resistance in plants against root and foliar diseases. For example, the plant growth-promoting rhizobacteria *Pseudomonas fluorescens* and *Serratia marcescens* can induce systemic resistance in cucumber to anthacnose [Wei, G., Kloepper, J. W., and Tuzun, S. 1991. Induction of systemic resistance of cucumber to *Colletotrichum orbiculare* by select strains of plant growth promoting rhizobacteria. *Phytopathology* 81:1508-1512], and the cucumber mosaic virus [Raupach, G. S., Liu, L. Murphy K. F, et al. 1996. Induced systemic resistance in cucumber and tomato against cucumber mosaic cucumovirus using plant growth-promoting rhizobacteria. *Plant Disease.* 80:891-894].

Capitalizing on the induction of plant defense mechanisms, extractions from a variety of non-plant-pathogenic microorganisms—fungi and bacteria primarily involved with composting—have been employed to fight a variety phytopathogenic microbes under the premise of inducing resistance following exposure to extracts of non-phytopathogenic microbes. Such formulations have been described in U.S. Pat. No. 6,326,016.

In fact, metabolites from microorganisms associated in the production of compost tea have been readily effective in controlling some of the most devastating *Xanthomonas* spp. related diseases such as citrus canker. This has been more successful as a preventative measure in healthy citrus trees [Ozores-Hampton, M. O. and Obreza, T. A. 2000. A composted waste use on Florida crops: A Review. International Composting Symposium, Nova Scotia]. Furthermore, evidence exists which suggests that *Pantoea agglomerans* strain E278Ar can induce systemic resistance against *X. campestris* pv. *armoraciae* induced leaf spot disease in radish [Han, D., Y., Colin, D. L., Bauer, W. D., and Hoitink, H. A. J. 2000. A rapid bioassay for screening rhizosphere microorganisms for their ability to induce systemic resistance. *Phytopathology* 90:327-332].

As early as 1991, a considerable number of studies have focused on the actions of such microorganisms to produce resistance of plants toward specific phytopathogens. The type of systemic resistance induced by nonpathogenic microorganism exposure to plants has been termed induced systemic resistance (ISR) [Kloepper, J. W., Tuzun, S., and Kuć, J. A. 1992. Proposed definitions related to induced disease resistance. *Biocontrol Sci. Technol.* 2:349-351]. This is different from systemic acquired resistance (SAR) which is induced by necrotizing plant pathogens [Delaney, T. P. 1997. Genetic dissection of acquired resistance to disease. *Plant Physiol.* 113: 5-12; and Ryals, J., Neuenschwander, U. H., Willits, M. G. et. al. 1994. Systemic acquired resistance. *Plant Cell* 8:1809-1819].

Based on this rapidly growing field of understanding both ISR and SAR, several synthetic compounds have been developed which elicit plant defense reaction. One such compound, acibenzolar-S-methyl (Actigard 50W, Bion 50WG, Syngenta, Basel Switzerland) has been developed. Such compounds have demonstrated limited success in controlling *X. axonopodis* pv. *vesicatoria* induced bacterial spot disease in tomatoes [Louws, F. J., Wilson, M., Campbell, H. L., et. al. 2001. Field control of bacterial spot and bacterial speck of tomato using a plant activator. *Plant Disease.* 85: 481-488]. Other activators do exist. However, a major concern regarding the use of synthetic activators is the long-term phytotoxicity and bioactivity in controlling the induction of disease resistance over time in field application.

Natural activators of plant resistance exist. Once such factor is riboflavin. Riboflavin has been demonstrated to act as an effective elicitor for systemic resistance, and as an activator in plants by inducing the a signal transduction pathway for the expression of pathogenesis-related genes [Dong, H. and Beer, S. V. 2000. Riboflavin induces disease resistance in plants by activating a novel signal transduction pathway. *Phytopathology* 90: 801-811]. Direct application of riboflavin as an elicitor for systemic resistance has been limited to laboratory experiments. Its exogenous use in the field on a variety of plants has not been set into formal practice at this time.

Likewise, silicon ($Si_2$) has been investigated regarding its role in initiating plant resistance to disease. Such actions are controversial [Werner D., and Roth R. 1983. Silica metabolism. Pages 683-694 in: Inorganic Plant Nutrition. A. Läuchi and R. L. Bieleski, eds. Sringer-Verlag, Berlin; and Epstein, E. 1994. The anomaly of silicon in plant biology. *Proc. Natl. Acad. Sci. U.S.A.* 91: 11-17]. However, such controversy revolves around passive mechanical protection of plants. Nonetheless, $Si_2$ has been shown to be effective in protecting certain dicots against fungal disease and demonstrate some aspect of SAR toward such invading pathogens [Bélanger, R. R., Bowen, P. A., Ehret, D. L. et al. 1995. Soluble silicon: Its role in crop and disease management of green house crops. *Plant Disease.* 79:329-336].

Moreover, Fawe et al. have provided evidence which suggest that $Si_2$ may offer protection of cucumber from *Pythium ultimum* by inducing cucumber production of the phytoalexins such as flavonol aglycone rhamnetin [Fawe, A., Abouu-Zaid, M., Menzies, J. G. et al. 1998. Silicon-mediated accumulation of flavonoid phytoalexins in cucumber. *Phytopathology* 88:396-401].

Despite the controversy surrounding the use of such agents for adding protection of plants from disease, the skilled practitioner can identify that such agents can be added to this invention. However, extracts used in our product from *Y. schidigera* are known to posses many plant growth promoting and plant protection stimulants [Zielgler, D. M. 1990. Flavin-containing monooxygenases: enzymes adapted for multisubstrate specificity. *Trends in Pharmacol. Sci.* 11: 321-324; Ziegler, D. M. 1993. Recent studies on the structure and function of multisubstrate flavin-containing monooxygenases. *Ann. Rev. Pharmacol. Toxicology* 33: 179-199; and Zhoa, Y., Christensen, S. K., Frankhauser, C., et al. 2001. A role for flavin monoxygenase-like enzymes in auxin biosynthesis. *Science* 291:306-309].

In relation to biological control, many *Trichoderma* spp. have been employed as biological control agents toward plant fungal diseases and have demonstrated the ability to elicit SAR to such pathogens. One such elicitor factor from the fungus *Trichoderma virens* has been identified and described in U.S. Pat. No. 6,242,420. However its field application is currently unresolved, and in principle it is directed toward fungal plant diseases associated with the rhizosphere.

Many fungi of the genus *Trichoderma* produce substances which kill or inhibit the growth of a variety of aerobic and anaerobic bacteria. Based on this principle, *T. virens* has been used as a mycoparasite and antibiotic-producing antagonist of plant pathogens, and has demonstrated to be an effective biological control agent against a variety of soil-borne root diseases [Reyes A. A. 1985. Suppression of *Fusarium* and *Pythium* pea root rot by antagonistic micro-organisms, *Phytoprotect.* 66:23-29]. Furthermore, intact cultures and spent culture medium from *T. virens* have been used as biological control agent against many phytopathogenic fungi as described by Tahvonen et al. in U.S. Pat. No. 5,968,504. A major problem in using this organism is based on the stability of its formulation; whereby, the viability of this organism is affected. Such formulations have been described in U.S. Pat. No. 4,724,147. Likewise, extracts from *Trichoderma* spp. have been employed with other added microbial extracts to induce resistance in plants against phytopathogenic microbes as described in U.S. Pat. No. 6,326,016.

Trichoderma spp. produce a considerable number of agents regarded as antibiotics which include gliotoxin, viridin, gliviron, and heptelidic acid. Heptelidic acid has been shown to be an effective antibiotic and antifungal agent. [Ghisalberti, E. L. and Sivasithamparan, K. 1991. Antifungal antibiotics produced by Trichoderma spp. Soil Biol. Biochem. 23:1011-1021].

Many Trichoderma spp. produce a variety of products which have profound antibiotic effects. One such class of metabolites are designated as peptaibols. These are short chain polypeptides ranging from 15 to 20 amino acids. Most of their amino acids are atypical such as hydroxyproline, isovaline, ethylnorvaline, and aminioisobutyric acid. As the name implies, peptaibols are generally regarded as protein antibiotics. The antimicrobial activity of peptaibols is thought to result from the ability to disrupt the integrity of lipid membranes—thus being more effective against gram-negative bacteria and fungi. To date, the most characterized peptaibols are disclosed from the fungi genera of Trichoderma and Emericellopsis.

In concern of this invention, peptaibols from T. harzianum include trichorzianins, trichokindins, trichorzines, and harzianins [El Hajji, M., Rebuffat, S., Lecommandeur, D., and Dodo, B. 1987. Isolation and sequence determination of trichorzianines A antifungal peptides from Trichoderma harzianum. Int J Peptide Protein Res. 29:207-215; Iida A, Sanekata, M., Fugita, T. et al. 1987. Fungal metabolites XVI. Structure of new peptaibols, trichorzins I-VI from the fungus Trichoderma harzianum. Int J Peptide Protein Res. 29:207-215; Rebuffat, S., El Hajji, M., Henning, P. et al. 1989. Isolation sequence, and conformation of seven trichorzianines B from Trichoderma harzianum. Int J Peptide Protein Res. 34:200-210; and Sawa, R., Mori, Y., Inuma, H. 1994. Harzianic acid, a new microbial antibiotic from a fungus. J. Antibiotics (Tokyo) 47: 731-732]. This invention capitalizes on the production of such metabolites from T. harzianum.

Trichoderma harzianum strains have been used as biological control agents against nematodes and fungal diseases in certain plants, and have been indicated as a plant promoting agent as cited in U.S. Pat. No. 6,475,772. Likewise, certain strains of T. harzianum have been exempted from requirements of a temporary tolerance and are employed as biological control agents for rhizosphere related fungal diseases in agricultural crops [Hasan, S. B. 2000. Trichoderma harzianum Rifai Strain T-39; Exemption from the Requirements of a Tolerance, Federal Register 65:121, pp. 38753-38757]. Nevertheless, a paucity exists within the literature regarding its applications to phyllosphere pathogens—in particular toward pathogens belonging to the genus Xanthomonas.

Employment of Trichoderma spp. as a biological control agent has been more successful against fungal phytopathogens. The major mechanism accounting for such actions include their microparasitism of both the invading pathogen and plant host evoking a cascade of events including the plant host cell protective interactions and direct degradation of the targeted fungal pathogen by the Trichoderma spp. employed.

Secreted chitanases and glucanases (β-1,3-glucanase and β-1,6-glucanase), secreted by Trichoderma spp. have been attributed to be involved in not only degrading other mycoparasites, but may play a role in eliciting plant cell defense mechanisms. Whereas such glucanases have been reported to lyse fungal and yeast walls, such enzymes have also been reported to lyse bacteria. [De La Cruz, J, Pintor-Toro, J. A., Benitez, T., and Llobell, A. 1995. Purification and characterization of an endo-β-1,6-glucanase from Trichoderma harzianum that is related to its mycoparasitism. J. Baceriol. 177: 1864-1871]. Nevertheless, the role of chitanases, β-1, 3-glucanase and β-1,6-glucanase in inducing host cell defense responses remain obscure.

A major problem with the use of many Trichoderma spp. is that they produce phytotoxins which can injure targeted host plants. One such toxin is viridin [Jones, R. W., W. T. Lanini, and J. G. Hancock. 1988. Plant growth response to the phytotoxin viridiol produced by the fungus Gliocladium virens. Weed Sci. 36:683-687; Weindling, R., and O. H. Emerson. 1936. The isolation of a toxic substance from the culture filtrate of Trichoderma. Phytopathology 26:1068; and Howell, C. R., and R. D. Stipanovic. 1984. Phytotoxicity to crop plants and herbicidal effects on weeds of viridiol produced by Gliocladium virens. Phytopathology 74:1346-1349]. In this respect, T. harzianum, also produces viridin.

Viridin is associated with sterol production in such fungi, and in 1994, Howell and Stipanovic demonstrated that viridin production in Gliocladium virens was significantly reduced when the fungus was grown in the presence of added steroid inhibitors. Likewise, such fungi not only demonstrated a reduction in viridin (as viridiol) production, but had decreased the phytotoxicity of this species [Howell, C. R., and Stipanovic R. D. 1994. Effect of sterol biosynthesis inhibitors on phytotoxin (viridin) production by Gliocladium virens in culture. Phytopathology 84:969-972]. This process of inducing the inhibition of viridiol is described in more detail in U.S. Pat. No. 5,882,915. In reference to this invention, the skilled microbiologist can quickly identify that such methods could be employed in this present invention. However, due to the extraction process employed in the present invention, recovered products from T. harzianum contain very little—if any—viridin and viridiol.

In reference to this invention, we originally used extracts from a strain of T. harzianum obtained from Venture Biodiscovery, Largo, Fla. This strain, MBMH-21 was first isolated from soil samples in Mission, Tex. However, with regards to this invention, we have found that a variety of T. harzianum strains work well. Such strains employed have included T. harzianum (American Type Culture Collection (ATCC) No. 20873). Other strains readily available from many distributers and fresh soil isolates of T. harzianum have also been employed in this invention.

The use of bioextracts and/or intact viable T. harzianum (or other Trichoderma spp.) are based on the phenomenon of induced systemic resistance as described above. As described above, such occurrence has been observed when nonpathogenic organisms are introduced into a host which triggers a cascade of defenses to fight off the invasions of pathogenic organisms. This stands to reason that exposure of a plant to a related non-phytopathogenic species may develop ISR to the related phytopathogen. In relation to this invention, we apply extracts from nonpathogenic Xanthomonas spp. Such employment is provided below in the detailed description of the invention. In relation to this invention, we employ extracts from *X. theicola* and *X. codiaei*. These organisms can be isolated from soil and certain plants. Furthermore, they can be purchased from such depository agencies as the ATCC.

Another component of our invention are extracts from the plant *Yucca schidigera*. Included in these extracts are saponins. Saponins are natural detergents found in many plants. Saponins have detergent or surfactant properties because they contain both water-soluble and fat soluble components. They consist of a fat-soluble nucleus, having either a steroid or triterpenoid structure, with one or more side chains of water-soluble carbohydrates. Saponins have been employed in a variety of food products, livestock feed, cosmetics, and beverages. Likewise, they have been indicated in therapeutic value in treating a variety of diseases

[Bingham, R., Bellew, B. A., Bellew J. G. 1975. Yucca plant saponin in the management of arthritis. *J Appl Nutr.* 27:45-50; Hartwell, J. L. 1976. Types of anticancer agents isolated from plants. Cancer Treat Rep. 60:1031-1067; Scarpato, R., Bertoli, A., Baccarati A., et al. 1998. Different effects of newly isolated saponins on the mutagenicity and cytotoxicity of the anticancer drugs mitomycin C and bleomycin in human lymphocytes. Mutat. Res. 420: 49-54].

Saponins have been employed as synergist in combination with aldehydes to control plant and animal pathogens as described in U.S. Pat. No. 5,639,794. Extracts from *Y. schidigera* and *Y. hedera* have been effective in controlling non-aquatic snails and slugs as identified in U.S. Pat. No. 5,290,557. It is evident that addition of saponins aid admixtures directed in controlling fungal and pest diseases among a variety of plants as cited within U.S. Pat. Nos. 5,639,794 and 6,482,770. However, to our knowledge, this invention is the first to apply *Y. schidigera* extracts (containing saponins and other against) against xanthomonad-related plant/crop diseases.

A major component to this invention involves principle extracts from certain *Xanthomonas* spp. Specific species employed in our invention include *X. theicola* and *X. codiaei*. Employment of these organisms is based on principles observed with the use of the outer membrane fractions of *P. fluorescens* to induce ISR in agriculture crops as described above. Both animal and plant host interactions with gram-negative bacteria pathogens are dependent on a cascade of events. Lipopolysaccharides are extremely effective in inducing both hypersensitivity reactions as well as ISR. The skilled practitioner will recognize that such extracts from more closely related targeted host specific diseases may be employed. However, our studies have provided evidence which suggest that the extracts from *X. theicola* and *X. codiaei* evoke hypersentitivity reactions (HR) in a variety of plants [i.e. citrus, tomatoes, and sugarcane]. Furthermore, the use of these relatively safe nonpathogenic *Xanthomonas* spp. are more environmentally friendly regarding possible transformation into an infectious phytopathogen.

SUMMARY OF THE INVENTION

This invention consists of reconstituting dried extracts from *T. harzianum, Y. schidigera, X. codiaei*, and *X. theicola* into a bioimmune-aggressin which provokes innate protection of plant cell hosts against phytopathogenic xanthomonads. Bioimmune-aggressin implies an agent which disseminates factors which provoke natural defenses of the invaded/exposed host plant to fight the invading pathogen. The extracts can be reconstituted in a variety of spreader/stickers for application as a spray, drip, or seed treatment. Whereas a variety of spreader/stickers may be employed, we have found that the non-ionic stick SS 9 (AgPro Systems, Inc.) works very well. This invention is intended to provide protection of susceptible plants from xanthomonad infections. Proposed protection of susceptible plants include—but not limited to—tomatoes, citrus (oranges, lime, grapefruit), carrots, sugarcane, catnip, and beans.

The principle of this invention is to provide an environmentally safe and nonphytotoxic biological control agent that protects and or reduces damage by phytopathogenic *Xanthomonas* spp. on agriculture crops and plants. "Biological control agent" is intended as control of phytopathogens via direct antipathogenic activity and/or induced resistance of the host plant to pathogen infestation using extracted natural products from a living organism. "Natural products" is intended as organic compound(s) of natural origin that is unique to one organism, or common to a small number of closely related organisms including secondary metabolites of the described organisms.

The invention accordingly comprises a composition of matter possessing the characteristics, properties, and the relation of components which will be exemplified in the compositions hereinafter described, and the scope of the invention will be indicated in the claims.

DETAILED DESCRIPTION OF THE INVENTION

Extraction and preparation of extracts from *T. harzianum, Y. schidigera, X. codiaei*, and *X. theicola* follow different methods; however, such extractions are commonly used by most practitioners in the field of microbiology. Likewise, the combinations of the dried extract materials follow a specific pattern for recombination into the final reagent.

A. Restrictive Analysis of Concerned Agents Used

1. Fungal Extraction

Initial strains of *T. harzianum* (MBMH-21) were obtained from Venture Biodiscovery, Inc., Largo, Fla. This strain was isolated from mud samples obtained within a citrus grove in Mission, Tex. during summer periods of 1998 and 1999. However, we have found that a variety of *T. haizianum* strains may be readily employed. Current production applications of this invention employ the use of *T. harzianum* from ATCC (No. 20873). *Trichoderma harzianum* strains used in this invention were identified by mycologists, and their morphology, chemistry, and growth characteristics were compared with type species of *T. harzianum* obtained from ATCC (Nos. 20873, 20848, and 20846)—which may also be employed in this invention.

All strains of *T. harzianum* used in this invention were maintained in both liquid and solid medium. Solid medium used was Potato-Dextrose Agar (PDA). For commercial use in our formulation, the organisms were grown under common fermentation processes in liquid medium consisting of Czapec medium supplemented with 10% (w/v) of dextrose and 0.1% (w/v) chitin (pH 6.8). Fermentation was carried out in 20 L autoclavable Nalgene bottles, under constant agitation at 28° C. The period of growth was dependent upon the initial inoculum size from cultures obtained from solid potato-dextrose agar (PDA). In principle, or primary inoculum was 2.8 g/L The skilled practitioner can readily identify that other fermentation media may be applied for large scale culturing of *T. harzianum*.

Following required incubation periods to obtain an initial stationary phase, mycelia were harvested by centrifugation at 6000×g, and the resulting supernatant was carefully separated from the pellets. The recovered pellets were washed extensively in 50 mM phosphate buffer. The recovered material was dried for 3 to 6 hours at 125° C. In parallel actions, recovered supernatants were combined and stored at 4° C. until used.

Step A. Extractions of Supernatant:

The recovered supernatant was subjected to ammonium sulphate precipitation (80% saturation) at 4° C., and the precipitate was recovered by centrifugation prior to exhaustive dialyzed against a 50 mM potassium acetate buffer (pH 5.5). The resulting dialyzed material was subjected to ethanol-precipitated pustulan according to the methods described by De La Cruz et al. [[De La Cruz, J, Pintor-Toro, J. A., Benitez, T., and Llobell, A. 1995. Purification and characterization of an endo-β-1,6-glucanase from *Trichoderma harzianum* that is related to its mycoparasitism. J. Baceriol. 177: 1864-1871]. Pulstan absorbed material was recovered by centrifugation, and the pellets were washed with a 70 mM phosphate buffer (pH 6.0), and resuspended in a 50 mM potassium acetate buffer supplemented with 1 mM phenylmethylsulfonyl fluoride and 1 mM sodium azide. The mixture was incubated overnight at 37° C. under constant agitation. Following pulstan digestion, the mixture was centrifuged at 12,000×g for 10 min. The clarified solution was then subjected to dialysis against a 25 mM imidiazole-HCl buffer (pH 7.4). The recovered dialyzed solution was concentrated 10-fold using an PM-100 Amicon membrane in an Amicon ultrafiltration unit using $N^2$ at 4° C. The recovered concentrated material was dried in vacuo and stored at −80° C. until required for glucanase activity. Assays for β-1,3-glucanase and β-1,6-glucanase were performed according to the methods described De La Cruz et al. [Ob cit.].

Step B: Extraction of Dried Mycelia:

Forty to 150 g (dry weight) of the material were frozen in liquid nitrogen and pulverized prior to subjecting the material to disruption with a tissue grinder. Two extractions were performed on the dried material. The material was added to 1 L of an organic solvent solution consisting of acetonitrile and ethanol (3:1) and incubated at room temperature for 2.5 to 4 hours prior to centrifugation. The recovered extractions were centrifuged at 30,000×g for 30 minutes, and the supernatant was carefully removed.

The supernatant was dried in vacuo. The dried residue was subjected to protein, carbohydrate, steroids, and lipid analysis following standard procedures [Burdon, R. H. and P. H. van Knippenberg (Eds.) Laboratory techniques In Biochemistry and Molecular Biology, Volume 17: Applications of HPLC in Biochemistry. 1987. Elsevier: New York]. Extracts were further subjected to analysis for viridiol following the methods of Jones and Hancock [Jones, R. W. and Hancock, J. G. 1987. Conversion of viridin to viridiol by viridin producing fungi. Can. J. Microbiol. 33:913-966]. Peptaibol analysis of dried extracts from *T. harzianum* cultures followed the methods described by Brükner [Brükner, H. 1984. Methods for the rapid detection, isolation and sequence determination of Peptaibols and other aib-containing peptides of fungal origin. *Chromatographia* 19: 188-199].

Chromatography was performed on an ISCO 2360 HPLC system integrated with an ISCO $V_4$ detector. Fractionation was performed on suggested columns of references using preferred mobile phase for elution as given in the aforementioned references. gliotoxin, viridin, viridiol, and heptelidic acid. Results of the analysis from recovered samples are given in Table 1.

2. Yucca Extraction Methods

Whereas the skilled practitioner will recognize that many extracts of *Y. schidigera* are commercially available, in our formulation, we prefer to utilize leaves and roots from young *Y. schidigera* (mean height approximating ≦1 m). Leafs and root samples from *Y. schidigera* are collected and supplied to us by Emerald Gardens, Willis, Tex.

Fresh leaves are chopped roughly in a blender with a minimal amount of water. Following this disruption, 100 mL of 95% ethanol is added, and the leaves are subjected to disruption again in blender at 4° C. for 20 minutes. Following this extraction, the homogenate is filtered through a Nos. 2 fluted Whatman filter, and the filtrate is subjected to centrifugation at 20,000×g for 20 minutes at 4° C. The resulting supernatant is removed and subjected to low temperature evaporation (30° C.) using a Büchi R-300 Rotavapor evaporator. The resulting residue is resuspended in 40% ethanol and stored at 4° C. until required.

Under similar methods, roots from *Y. schidigera* are coarsely chopped with a knife, then placed in a shearing blender with equal volumes of methanol:butanol (1:1 v/v). Following homogenation, the contents are subjected to centrifugation and filtered as described above. Following filtration, the resulting filtrate is subjected to evaporation as described above. The residue is recovered with a minimal amount of ethanol, and stored at 4° C. until required.

Our principle interest in such extractions concerns steroidal saponins. Whereas the practitioners in the art may identify a considerable number of methods for qualitative analysis of saponin moieties, we followed the methods of Wei [Wei, J. 1998. Determination of steroidal saponins in *Rhizoma pridis* by UP-HPLC. *Yak Xu Bad* 33:465-468]. Chromatography was performed on an ISCO system described above, using a Symmetry C8 column. The mobile phase for isolation was acetonitrile-water (42:58 v/v) at a flow rate of 1.0 mL/min. The effluents were monitored at 203 nm.

A considerable number of saponins were recovered. Based on analysis (which are still being performed) several known saponins have been identified, and characteristically do not differ from published reports on recovered saponins of *Y. schidigera*. Saponins used in this invention are given in Table 2.

*Yucca schidigera* contains many active ingredients besides saponins. We are currently examining these bioactive compounds in attempts to further support the intention of this invention.

3. *Xanthomonas* spp. Extractions

In relation to this invention, we utilize *X. theicola* and *X. codiaei*. Theses microbes are readily available from many cell repository agencies. In this invention, we focused on using extracts from bacterial membrane fragments following standard methods. *Xanthomonas* spp. employed were first grown on solid 73 YGC agar. For large scale production, the organisms were separately grown under fermentation in liquid medium consisting of 10 g/L yeast extract, 10 g/L glucose, 5 g/L $CaCO_3$, and 0.1 g/L casein (pH 6.8). Whereas other liquid media may be employed in this fermentation process, the medium employed for this invention works very well. Fermentation took place in Nalgene bottles as described above, and initial inoculum consisted of 3.1 g/L of the concerned bacterium obtained from YGC agar growth. Fermentation took place at 25° C. under constant agitation. The concerned bacteria were recovered by centrifugation at 4,000×g for 20 minutes at 4° C. The recovered bacteria were washed twice with a 10 mM HEPES buffer (pH 7.4), and recovered pellets were stored at −80° C. prior to membrane extractions following the methods of Vesy et al. [Vesy, C. J., Kitchens, R. L., Wolfbauer, J. J. et al. 2000. Lipopolysaccharide-binding protein and phospholipid transfer protein release lipopolysaccharides from gram-negative bacterial membranes. *Infect. Immun.* 68: 2410-2417]. Recovered lipid-related material was subjected to analysis following established methods [Burdon, R. H. and P. H. van Knippenberg (Eds.) 1987. Laboratory techniques In Biochemistry and Molecular Biology, Volume 17: Applications of HPLC in Biochemistry. Elsevier: New York; and Work, T. S. and E. Work (Eds.) 1982. Laboratory techniques in Biochemistry and Molecular Biology: Techniques of Lipidology. Elsevier: New York].

In parallel studies, lipopolysaccharides (LPS) were identified from both *Xanthomonas* spp. employed following hot phenol extraction methods described by Severn et al. [Severn, W. B., Kelly, R. F., Richards, J. C., and Whitfield, C. 1996. Structure of the core oligosaccharide in the serotype O8 lipopolysaccharide from *Klebsiella pneumoniae*. *J. Bacteriol.* 178: 1731-1741].

Through our process of extractions, a considerable number of lipids, phospholipids, and lipopolysaccharides were recovered. Since lipopolysaccharides (LPS) are known to exacerbate pathogen aggressions, we focused on the characterization of the LPSs from *Xanthomonas* spp. employed in this invention. Interpretation of the recovered LPS was limited by the fact that the LPS identified were natural constituents of the *Xanthomonas* spp. and not a purified chemical. Whereas some of the LPS constituents of some *Xanthomonas* spp. have been identified [Ojanen, T., Helander, I. M, Haahtela, H., et al. 1993. Outer membrane proteins and lipopolysaccharides in pathovars of *Xanthomonas campestris*. *Appl. Environ. Microbiol.* 59:4143 (Abstr.)]. Results of identifiable components are given in Table 3; however, analysis for more specific products are currently being investigated.

TABLE 1

Concentrations of selected components from *Trichoderma harzianum* (ATCC 20873).

A. Supernatant Extraction

| Unknown Proteins > 100000 Da (mg) | Unknown Proteins < 100000 Da (mg) | Chitinases (U/mg) | β-1,3-glucanase (U/mg) | β-1,6-glucanase (U/mg) | Protease (U/mg) | Glycolipids¶ (mg) |
|---|---|---|---|---|---|---|
| 14.3 | 22.4 | 2.1 | 5.1 | 3.2 | 6.2 | 8.7 |

B. Dried Mycelia Extraction

| Viridiol (µg) | Gliotoxin (µg) | Heptelidic Acid (µg) | Trichorzianins (µg) | Trichorzines (µg) | Harzianins (µg) | Unknown¶ Lipids (µg) |
|---|---|---|---|---|---|---|
| ND‡ | 86.4 | 31.2 | 19.3 | 16.2 | 9.3 | 41.4 |

¶ = Material is still be analyzed.
‡ = Substance not detected.

TABLE 2

Saponins recovered in extracts of leaves and roots of *Yucca schidigera*

| Source | Compound | Percent Based On Total Recovery |
|---|---|---|
| Leaf | sarsapogenin | 0.2% |
| | gloriogenin | 0.6% |
| | markogenin | 0.01% |
| | furostanal | ND‡ |
| Root | sarsapogenin | 53.2% |
| | gloriogenin | 23.8% |
| | markogenin | 2.2% |
| | furostanal | 2.1% |

‡ = Not detected

B. Formulation of Bioimmune-Aggressin Compound ("The Invention")

The concerned invention involves appropriate mixing of the biological extracts of concern as follows:

1. *Trichoderma harzianum* preparation: The first step in this process is to grow large quantities of *T. harzianum* underfermentation conditions as described above. The organisms are grown until an initial stationary phase of growth is reached as determined by protein concentrations. Mycelia are harvested by centrifugation as previously described. The recovered pellet is frozen in liquid nitrogen and pulverized prior to subjecting the material to disruption with a tissue grinder as described above. The homogenates are extracted with acetonitrile and ethanol (3:1) using multiple samples of recovered material at a ratio 400 to 600 g (wet weight) of homogenate per liter of solvent. The extrac-

TABLE 3

Combined Lipid Extracts From *Xanthomonas theicola* and *Xanthomonas codiaei*.

A. *Xanthomonas theicola*

| | Mol % Total Fatty acids[a] | | | | | | | |
|---|---|---|---|---|---|---|---|---|
| Lipid Component | i14:0 | 14:0 | i15:0 | 15:0 | i16:0 | 16:0 | 18:0 | 18:2 |
| Neutral Lipids | 4 | | 3 | 2 | 6 | 5 | 1 | 1 |
| Phospholipids | 14 | 2 | 13 | 6 | 44 | 2 | 9 | 3 |
| Cardiolipids | 22 | | 23 | 6 | 1 | | 2 | 1 |
| Phospatidylethanolamine | 26 | 1 | | 4 | 43 | 2 | 4 | 6 |
| Phosphatidylserine | | | 18 | | 68 | 2 | 23 | 9 |
| Lipopolysaccharide (Approx. 2.7% yield dry weight of cells) | Primary Neutral Sugar Composition: Xylose and 6-deoxy-3-O-methyl hexose | | | | | | | |

B. *Xanthomonas codiaei*

| | Mol % Total Fatty acids[a] | | | | | | | |
|---|---|---|---|---|---|---|---|---|
| Neutral Lipids | 6 | | 2 | 3 | 8 | 6 | 5 | 2 |
| Phospholipids | 18 | | 11 | 9 | 32 | 2 | 11 | 4 |
| Cardiolipids | 17 | 3 | 16 | 4 | 23 | 1 | 14 | 1[i] |
| Phospatidylethanolamine | 19 | 2 | 1 | 8 | | 5 | 3 | 8 |
| Phosphatidylserine | | 1 | 7 | 1 | 43 | 6 | 18 | 3 |
| Lipopolysaccharide (Approx. 3.1% yield dry weight of cells) | Primary Neutral Sugar Composition: Xylose and 6-deoxy-3-O-methyl hexose | | | | | | | |

[a] Data presented as moles % of total identified fatty acids.
i = iso tion is made under constant agitation for up to five hours. The recovered extractions were centrifuged at 30,000×g for 30 minutes at 4° C. and the supernatant was carefully removed. The recovered supernatants are combined and dried in vacuo. The material (herein known as $TH_M$) is maintained in a dried condition until employed in the formulation as described below.

2. *Yucca schidigera* extract preparation: Leaves and roots from *Y. schidigera* are disrupted as described above. Briefly, the 60 to 90 g of chopped leaves were suspended in a minimal amount of water prior to disruption at 4° C. in a blinder blender. One hundred mL of 95% ethanol is added, and the leaves are subjected to disruption again in blender at 4° C. for 20 minutes. Following this extraction, the homogenate is filtered through a Nos. 2 fluted Whatman filter, and the filtrate is subjected to centrifugation at 20,000×g for 20 minutes at 4° C. The resulting supernatant is removed and subjected to low temperature evaporation (30° C.) using a Büchi R-300 Rotavapor evaporator. The resulting dried material (herein known as $YS_L$) was stored until employed in the final formulation.

Under similar methods, roots from *Y. schidigera* were coarsely chopped with a knife, then placed in a shearing blender with equal volumes of methanol: butanol (1:1 v/v). Following homogenation, the contents are subjected to centrifugation and filtered as described above. Following filtration, the resulting filtrate is subjected to evaporation as described above. The recovered residue (herein known as $YS_R$) was stored dried until required in the final formulation.

3. *Xanthomonas* spp. preparation: *Xanthomonas* theicola and *X. codiaei* were grown separately under a fermentation process described above. Bacteria was harvested by centrifugation, and recovered pellets from each species were separately disrupted in a French press. The recovered materials were combined and extracted in acetonitrile: ethanol (3:1) for 4 to 6 hours under constant agitation. The extraction was centrifuged and the resulting supernatant was dried in vacuo as described previously. The recovered residue (herein known as $XS_E$) was stored dried until required in the final formulation.

Various formulations of the product was manipulated to identify concentrations which were effective in preventing or treating Xanthomonad infections in controlled laboratory experiments. Formulations varied as follows:

| | |
|---|---|
| ##$TH_M$:$YS_L$:$YS_R$:$XS_E$##: 1:1:1:1 (dry w/w/w) | Formulation I |
| ##$TH_M$:$YS_L$:$YS_R$:$XS_E$##: 0.5:1:1:1 (dry w/w/w) | Formulation II |
| ##$TH_M$:$YS_L$:$YS_R$:$XS_E$##: 1:1:0.5:0.5 (dry w/w/w) | Formulation III |
| ##$TH_M$:$YS_L$:$YS_R$:$XS_E$##: 1:0.5:0.5:1 (dry w/w/w) | Formulation IV |
| ##$TH_M$:$YS_L$:$YS_R$:$XS_E$##: 0.5:0.1:0.2:1 (dry w/w/w) | Formulation V |
| ##$TH_M$:$YS_L$:$YS_R$:$XS_E$##: 0.5:0.1:0.1:1 (dry w/w/w) | Formulation VI |

The above formulas of the invention were mixed according to the given ratios. The formulas were suspended for final use in selective sticker/spreaders. We have had great success with SS 9 (AgroPro Systems, Inc.); however, we have utilized other sticker/spreaders. Effective concentrations for each formula which did not produce any observed phytotoxicity were determined as follows:

| | |
|---|---|
| 0.2 g to 1 g per gallon of spreader/sticker | Formulation I: |
| 0.2 g to 1 g per gallon of spreader/sticker | Formulation II |
| 0.3 g to 2 g per gallon of spreader/sticker | Formulation III |
| 0.2 g to 2 g per gallon of spreader/sticker | Formulation IV |
| 0.5 g to 5 g per gallon of spreader/sticker | Formulation V |
| 0.5 g to 5 g per gallon of spreader/sticker | Formulation VI |

Formulas are added to the spreader/sticker and agitated by hand. Most formulas readily dissolve in SS 9; however, Formula 1 at concentrations approaching 1 g/gallon of SS 9 resulted in the formation of a considerable amount of foaming. However, this can be reduced by the addition of acceptable anti-foaming agents.

Phytotoxicity Testing

Xanthomonads infect a considerable number of agriculture crops. Our principle interest is using this invention to afford protection on a variety of devastating xanthomonad infections. Therefore, we have been spraying various formulations of our invention on a variety of crops such as: tomato (*Lycopersicon esculentum*); orange trees (*Citrus sinensis*); grapefruit trees (*Citrus paradisi*); carrots (*Daucus carota*); lettuce (*Lactuca sativa*); bell pepper (*Capsicum annuum*); and more recently sugarcane (*Saccharum officinarum*).

Phytotoxic studies are still ongoing. Cultivars of these plants are sprayed monthly with various formulations of our invention on separate cultivars for each formulation. Such testing is seasonal, and considerable characteristics are being examined. Whereas fall and spring exposure of both young and older grapefruit and orange trees have not demonstrated any evidence of decreased fruit production or growth rates from the experimentals compared to controls, this study is still under progress.

Likewise spring and fall spraying of bell peppers, carrots, and lettuce have not demonstrated any ill-effects on the growth or production of these vegetables. Some evidence suggests that in the case of peppers, production yields appear to be higher. However, such studies are ongoing.

EXAMPLE 1

In Vitro Screening of Hypersensitivity Responses

Hypersensitivity responses toward this invention and challenges of pathogens were performed on *Citrus* spp. protoplasts. Callus protoplast were derived from shoots of *Citrus sinensis, C. paradisis,* and *C. limon* and routinely prepared in our laboratory following established procedures [Kyte, L and Kleyn, J (eds.) 1996. Plants from test tubes: An introduction to microporpagation. $3^{rd}$ Edition. Timber Press: Portland, Oreg.]. Callus-derived cells derived from explanted material of desired *Citrus* spp., and protoplast are formed from the callus-cell cultures following digestion with 3% cellulase; 0.5% macerase in solution of 0.5 M mannitol and sucrose having a final osmotic pressure of 825 m mole/kg. Recovered protoplast were grown in KM8p protoplast medium.

Freshly isolated protoplast (<48 hours after recovery) were used for both experimental and control studies. Selected cultures of desired protoplasts were exposed to various concentrations of different formulations and different concentrations of active ingredients. Likewise, Tween 80, amphotericin B and riboflavin were also employed to identify their ability to release hydrogen peroxide ($H_2O_2$)

from protoplast as positive and negative controls. Hydrogen peroxide production was measured in the culture medium of experimental and controls following established procedures [Jabs, T., Tschöpe, M., Colling, C., et al. 1997. Elicitor-stimulated ion fluxes and $O_2^-$ from oxidative burst are essential components in triggering defense gene activation and phytoalexin synthesis in parsley. *Proc. Natl. Acad. Sci. USA* 94:4800-4805] by measuring chemiluminescence produced by ferricyanide-catalyzed luminol oxidation. Viability of protoplast was determined by fluorescein diacetate and propidium iodide staining. Protoplasts from *C. sinensis, C. paradisis*, and *C. limon* where employed in this study. Our invention did produce a relatively considerable amount of $H_2O_2$ into the culture medium of the protoplast. For the most part, results among the protoplast employed were not too dissimilar between the different protoplast cultures used. However, for Example 1 of this invention we present the results of the study utilizing protoplasts from *C. sinensis*. Results of $H_2O_2$ production are given in Table 4.

Figure 1:
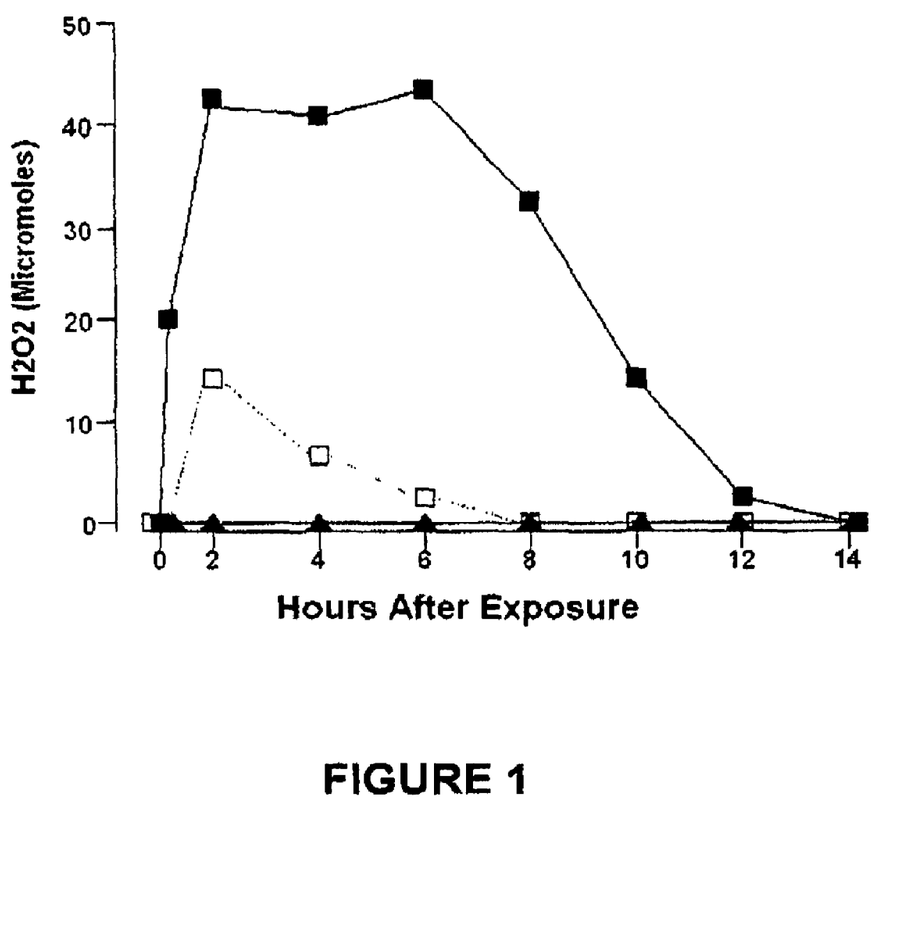

Extracts of the pathogen *X. axonopodis* [pv.] *citri* (XacE) [obtained from Dr. Marion Levy, University of Texas] at a final concentration of 60 μg/mL based on known protein concentration of the XACE. Hydrogen peroxide release was determined as described above. Results are given in Graph 1.

TABLE 4

Hydrogen peroxide accumulation in the medium of *Citrus sinensis* protoplast following exposure to the invention and challenges for various time periods.

| AGENT | $H_2O_2$ equivalents (μM)/Hours after 0.24 | 0.5 | 1 | 2 | 4 | 8 | 12 | 16 |
|---|---|---|---|---|---|---|---|---|
| Tween 80 (60 μM)[§] | ND[‡] | ND | ND | ND | ND | ND | ND | ND |
| Amphotericin B (30 μM) | 3.1 | 4.2 | 3.0 | 1 | ND | ND | ND | ND |
| Riboflavin (50 μM) | ND | 2.3 | 2.0 | ND | ND | ND | ND | ND |
| SS 9 (100 μL/mL) | ND | ND | ND | ND | ND | ND | ND | ND |
| Formula V in SS 9 (10 μg/mL) | 10.3 | 20.2 | 33.4 | 28.1 | 23.2 | 21.4 | 6.5 | ND |
| Formula V (10 μg/mL) | 11.4 | 21.4 | 36.2 | 33.4 | 28.3 | 20.4 | 9.8 | 3.4 |
| *T. harzianum* extract (40 μg/mL) | 9.4 | 16.5 | 16.3 | 11.4 | 8.3 | 4.2 | 2.3 | ND |
| *Y. schidigera* extracts combined (40 μg/mL) | ND | 3.3 | 4.1 | 4.0 | 3.2 | 2.1 | ND | ND |
| *X. codiaei*; *X. theicola* extracts (40 μM/mL)[¶] | 4.0 | 8.3 | 5.2 | 3.4 | 2.2 | ND | ND | ND |

[‡]= ND; not detectable.
[¶]= Based on lipid concentration.
[§]= Based on specific gravity.

Extracts of the pathogen *X. axonopodis* [pv.] *citri* (XacE) [obtained from Dr. Marion Levy, University of Texas] at a final concentration of 60 μg/mL based on known protein concentration of the XacE. Hydrogen peroxide release was determined as described above. Results are given in FIG. 1.

Whereas the use and distribution of *Xanthomonas* spp. for research are highly restricted by the USDA Animal Health and Plant Inspection Service, we could only test our invention with xanthomonad diseases readily available. Currently, we have permit applications in to test our product against citrus canker and other sever *Xanthomonas*-related diseases.

Likewise, a variety of the formulations described above have been employed in such studies. However, data from Formula V are only presented. Other formulas presented similar results; however, Formula V has demonstrated less foaming problems when added to spreading and sticking agents employed in our studies.

EXAMPLE II

Control of Xanthomonad-Induced Leaf Spot Disease of *Nepeta cataria*

Catnip (*Nepeta cataria*) is subject to leaf spot disease by a variety of bacteria including *X. campestris*. In order to test the effectiveness of our admixture on xanthomonad-disease, we used a catnip model. In a controlled green house located in Willis, Tex., we planted 28, 2 month old *Neptea cafaria* in pots. The plants were divided into experimental and control groups each having 4 plants per group. Forty-eight hours prior to experimentation, the groups were placed in saturated dew chambers.

*Xanthamonas campestris* was grown under agitation in nutrient broth for 48 hours, and diluted to a suspension of $10^6$ CFU/mL as determined by plating methods. Tween 20 was added the bacterial suspension at a final concentration of 0.5%. Using a hand-held mister, plants were sprayed with the bacterial mixture. Plants were monitored every other day for evidence of disease.

Within two weeks, small brown speaks characteristic of leaf spot were observed on several of the experimental plants. Following a week later, the size of the speaks grew to larger angular brown spots resembling characteristics common observed in leaf spot disease of catnip. Sets were separated to allow treatment at various stages of spot identification to considerable necrosis.

Following observation of disease characteristics and advancement, we utilized our admixture with the following conditions. Formula V was prepared whereby its final concentration was in 0.5 g of formula per gallon of SS 9. Control plants were treated with SS-9 only. Following this study, plants and their plastic pots were incinerated; potted soil from all plants were autoclaved, and dew chambers were disinfected. Results are presented in Table 5.

As shown in Table 5, early signs of infection sprayed with Formula V stopped the disease within 2 weeks of application. No signs of the disease in these plants could be observed for one month following its treatment. Likewise, plants expressing limited necrosis prior to exposure to Formula V demonstrated a reduction in the infection and a healing process within 2 weeks after spraying with Formula V. Within 4 weeks following treatment, no apparent disease was observed, and brown patches were not observed.

Likewise, catnip samples expressing a higher degree of necrosis were afforded protection with Formula V. Within 3 weeks following treatment with Formula V, a marked increase in necrosis healing was observed, and complete recovery was observed within 4 weeks after spraying of Formula V.

In contrast, infected catnip plants receiving only SS-9 were not afforded protection. As shown in Table 5, the disease progressed very rapidly whereby the control groups were terminated due to high progression of the disease.

In parallel studies, a total of eight, 2 month old plants were sprayed with Formula V prepared as described above. After one week of spraying, the plants were infected *X. campestris* following the concentrations and conditions given above. All experimental and controls were terminated and destroyed as given above. Results from this study are presented in Table 6.

As shown in Table 6, catnip plants sprayed with Formula V one week prior to infection with *Xanthamonas campestris* were afforded protection against this bacteria. In contrast, plants sprayed with SS-9 alone were not protected from the progression of the disease.

EXAMPLE 3

Control of Xanthomonad Killing of *Poa Annua*

In addition to testing the effects of xanthomonad infection of catnip, we utilized the annual blue grass, *Poa annua*, to test the effects of our admixture on this grass' infection with *Xanthomonas campestris* [pv.] *poannua* (obtained as XPO from Eco Soil Systems). In this study, *Poa annua* were grown in open Phytatray (Sigma). The trays were separated into controls (N=10 trays) and experimental groups (N=10 trays). After one month of growth, experimental trays were sprayed with *X. campestris* [pv.] *poannua* according to manufacture's directions. Following infection, we waited for the appearance of injury to the grass, then sprayed them with Formula V as given above. Controls received either no Formula V or SS-9 only. Results are presented in Table 7.

As shown in Table 7, Formula V protected the grasses from progression of the disease. The effect on grass expressing minimal injury were afforded protection within one week after spraying with Formula V. Likewise, plants expressing moderate injury demonstrated a healing process and lack of disease within 2 weeks following exposure to Formula V. Plants demonstrating higher degrees of injury from *X. campestris* [pv.] *poannua* were free of disease within three weeks following exposure to Formula V. In contrast, blue grass expressing moderate disease symptoms prior to spraying with SS-9 only were afforded no protection from *X. campestris* [pv.] *poannua.*

In parallel studies, we sprayed healthy blue grass with Formula V one week prior to infection with *X. campestris* [pv.] *poaannua* in order to determine prophylactic protection of the blue grass from this pathogen by our invention. Results of the experiments are presented in Table 8.

As shown in Table 8, grasses sprayed with Formula V prior to exposure to the pathogen were afforded protection. In contrast, grasses sprayed with SS-9 only were not protected and demonstrated progression of the disease as compared to infected plants not sprayed with any other formula except those containing the pathogen.

TABLE 5

Control of xanthomonad infection in catnip using invention admixture Formula V

| Disease Condition | Disease Observation Following Weeks After Spraying of Admixture | | | | | |
|---|---|---|---|---|---|---|
| Experimental | 1 | 2 | 3 | 4 | 5 | 6 |
| 1+ | 1+ | np[¶] | np | np | np | np |
| 2+ | 2+ | 1+ | 1+ | np | np | np |
| 3+ | 3+ | 3+ | 2+ | np | np | np |
| Controls | | | | | | |
| No Disease (non-infected) | np | np | np | np | np | np |
| 3+ SS-9 Only | 3+ | 3+ | 3+ | 3+ | Terminated[‡] | Terminated |
| 2+ SS-9 Only | 2+ | 2+ | 3+ | 3+ | Terminated | Terminated |
| 1+ SS-9 Only | 1+ | 1+ | 1+ | 2+ | 2+ | Terminated |

Potted plants were sprayed with pathogen and maintained until desired condition developed prior to spraying.
Reactions were analyzed as follows:
3+ Excessive Necrosis;
2+ limited water-soaking necrosis;
¶np = no progression of disease with evidence of healing.
‡= denotes removal and incineration of plant due to advance stages of disease.

TABLE 6

Effectiveness of admixture in retarding *X. campestris* infection in catnip

| Condition | Observation Following Inoculation with *X. campestris Mixture* Weeks after Spraying | | | | | |
|---|---|---|---|---|---|---|
| | 2 | 4 | 6 | 8 | 10 | 12 |
| Plants Sprayed Form. V | np | np | np | np | np | np |
| Plants Sprayed SS-9 only | np | 1+ | 1+ | 2+ | 3+ | np |
| Plants Not Sprayed | 1+ | 2+ | 3+ | 3+ | Terminated[¶] | |

Potted plants were sprayed with bacteria one week after plants received saturation with Formula V.
Reactions were analyzed as follows:
3+ Excessive Necrosis;
2+ limited water-soaking necrosis;
1+ limited spot observations;
np = no progression of disease with evidence of healing.
¶= denotes removal and incineration of plant due to advance stages of disease.

TABLE 7

Control of xanthomonad infection in *Poa annua* using admixture Formula V

| | Disease Observation Following Weeks After Spraying of Admixture | | | |
|---|---|---|---|---|
| | 1 | 2 | 3 | 4 |
| Experimental | | | | |
| 1+ | np | np | np | np |
| 2+ | 1+ | np | np | np |
| 3+ | 2+ | 1+ | np | np |

TABLE 7-continued

Control of xanthomonad infection in *Poa annua* using admixture Formula V

| | Disease Observation Following Weeks After Spraying of Admixture | | | |
|---|---|---|---|---|
| | 1 | 2 | 3 | 4 |
| Control | | | | |
| Non-infected | np | np | np | np |
| Infected SS-9 only sprayed | 1+ | 2+ | Terminated¶ | |

Planted grass sprayed with pathogen and maintained until desired pathological changes developed prior to spraying with Formula V.
Reactions were analyzed as follows:
3+ Excessive browning with necrosis;
2+ advanced browning and wilting,
1+ limited browning observed;
np = no progression of disease with evidence of healing.
¶= denotes plants death.

TABLE 8

Effectiveness of admixture in retarding xanthomonad infections in *Poa annua*

| | Admixture Protection of Grass Following Inoculation with *X. campestris* [pv.] *poannua* Weeks following Infection | | | | |
|---|---|---|---|---|---|
| Condition | 1 | 2 | 3 | 4 | 5 |
| Plants Sprayed Formula V | np | np | np | np | np |
| Plants Sprayed SS-9 only | 1+ | 2+ | 3+ | Terminated¶ | |
| Plants Not Sprayed | 1+ | 1+ | 2+ | 3+ | Terminated |

Planted grass were sprayed with Formula V prior to inoculation with pathogen.
Reactions were analyzed as follows:
3+ Excessive browning with necrosis;
2+ advanced browning and wilting;
1+ limited browning observed;
np = no progression of disease with evidence of healing.
¶= denotes removal and incineration of plant due to advance stages of disease.

It will thus be seen that the objects set forth above, among those made apparent from the preceding description, are efficiently attained, and since certain changes may be made in the above composition of matter without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Particularly, it is to be understood that in said claims, ingredients or compounds recited in the singular are intended to include compatible mixtures of such ingredients wherever the sense permits.

Now that the invention has been described,

What is claimed is:

1. A composition for treating phytopathogenic *Xanthomonas* spp. infections in agriculture crops, said composition comprising about 0.5-1.0 *Trichoderma harzianum* extract by weight, about 0.1-1.0 *Yucca schidigera* root extract by weight, about 0.1-1.0 *Y. schidigera* leaf extract by weight, and about 0.5-1.0 nonphytopathogenic extract of *Xanthomonoas theicola* and X. *codiaei* by weight.

2. A composition as in claim 1 comprising about 1.0 *T. harzianum* extract by weight, about 1.0 *Y. schidigera* root extract by weight, about 1.0 Y. schidigera leaf extract by weight, and about 1.0 nonphytopathogenic extract of *X. theicola* and *X. codiaei* by weight.

3. A composition as in claim 1 comprising about 0.5 *T. harzianum* extract by weight, about 1.0 *Y. schidigera* root extract by weight, about 1.0 *Y. schidigera* leaf extract by weight, and about 1.0 nonphytopathogenic extract of *X. theicola* and *X. codiaei* by weight.

4. A composition as in claim 1 comprising about 0.5 *T. harzianum* extract by weight, about 0.5 *Y. schidigera* root extract by weight, about 1.0 *Y. schidigera* leaf extract by weight, and about 0.5 nonphytopathogenic extract of *X. theicola* and *X. codiaei* by weight.

5. A composition as in claim 1 comprising about 1.0 *T. harzianum* extract by weight, about 0.5 *Y. schidigera* root extract by weight, about 0.5 *Y. schidigera* leaf extract by weight, and about 1.0 nonphytopathogenic extract of *X. theicola* and *X. codiaei* by weight.

6. A composition as in claim 1 comprising about 0.5 *T. harzianum* extract by weight, about 0.2 *Y. schidigera* root extract by weight, about 0.1 *Y. schidigera* leaf extract by weight, and about 1.0 nonphytopathogenic extract of *X. theicola* and *X. codiaei* by weight.

7. A composition as in claim 1 comprising about 0.5 *T. harzianum* extract by weight, about 0.1 *Y. schidigera* root extract by weight, about 0.1 *Y. schidigera* leaf extract by weight, and about 1.0 nonphytopathogenic extract of *X. theicola* and *X. codiaei* by weight.

8. A method for treating phytopathogenic *Xanthomonas* spp. infections in agriculture crops, said method comprising applying the composition of claim 1 to the infected crop by spraying.

9. A method for enhancing the resistance of agriculture crops to phytopathogenic *Xanthomonas* spp. infections, said method comprising applying the composition of claim 1 to the crop by spraying.

* * * * *